US012797645B2

(12) United States Patent
Gershonowitz

(10) Patent No.: US 12,797,645 B2
(45) Date of Patent: Nov. 17, 2026

(54) ULTRASOUND BASED TISSUE TREATMENT

(71) Applicant: POLLOGEN LTD., Tel Aviv (IL)

(72) Inventor: Amikam Gershonowitz, Tel Aviv (IL)

(73) Assignee: POLLOGEN LTD., Tel Aviv (IL)

( * ) Notice: Subject to any disclaimer, the term of this patent is extended or adjusted under 35 U.S.C. 154(b) by 0 days.

(21) Appl. No.: 19/259,158

(22) Filed: Jul. 3, 2025

(65) Prior Publication Data

US 2025/0325841 A1 Oct. 23, 2025

Related U.S. Application Data

(63) Continuation of application No. PCT/IL2024/050008, filed on Jan. 2, 2024.

(60) Provisional application No. 63/437,167, filed on Jan. 5, 2023.

(51) Int. Cl.
*A61N 7/00* (2006.01)

(52) U.S. Cl.
CPC ........ *A61N 7/00* (2013.01); *A61N 2007/0034* (2013.01)

(58) Field of Classification Search
CPC .......................... A61N 7/00; A61N 2007/0034
See application file for complete search history.

(56) References Cited

U.S. PATENT DOCUMENTS

| | | | | |
|---|---|---|---|---|
| 2003/0060735 | A1 * | 3/2003 | Coffey ..................... | A61N 7/00 601/2 |
| 2008/0281237 | A1 | 11/2008 | Slayton et al. | |
| 2019/0262634 | A1 | 8/2019 | Barthe et al. | |
| 2020/0222728 | A1 * | 7/2020 | Khokhlova .............. | A61N 7/02 |

OTHER PUBLICATIONS

Casarotto RA, Adamowski JC, Fallopa F, Bacanelli F. Coupling agents in therapeutic ultrasound: acoustic and thermal behavior. Arch Phys Med Rehabil. Jan. 2004;85(1):162-5. (Year: 2004).*
Search Report and Written Opinion—corresponding PCT Application No. PCT/IL2024/050008, dated Mar. 4, 2024, 24 pages.

* cited by examiner

*Primary Examiner* — Chao Sheng
(74) *Attorney, Agent, or Firm* — ISUS Intellectual Property PLLC; Anthony Jason Mirabito

(57) ABSTRACT

A device for insertion between tissue to be treated and an ultrasound device. The device comprises at least one region that is configured to heat to a predetermined temperature range, due to ultrasound energy of predetermined properties interacting therewith. When the at least one region is positioned in vicinity of the tissue, the at least one region heats the skin tissue, by heat diffusion, according to a heating profile defined by a temperature range and a tissue depth.

7 Claims, 3 Drawing Sheets

ULTRASOUND BASED TISSUE TREATMENT

RELATED APPLICATIONS

This application is related to US Provisional Application 63/437,167 filed Jan. 5, 2023, and PCT application No. PCT/IL2024/050008 filed Jan. 2, 2024, both entitled "Ultrasound Based Tissue Treatment Device" to which applications priority is hereby claimed and the entire contents of which are herein incorporated by reference.

TECHNOLOGICAL FIELD

The present invention is in the aesthetic field and relates specifically to tissue treatment, such as skin tissue treatment for tightening and rejuvenation.

BACKGROUND

A variety of techniques for non-invasive skin tissue treatment for aesthetic purposes are prevalent, such as those based on optical, radiofrequency and/or ultrasound technologies. The fundamental principle of operation of these different technologies is similar and involves heating and destroying old skin tissue to stimulate and enable the body to produce healthy new skin tissue that will look nicer, younger, and tighter. Ultrasound-based therapy utilizes deposition of focused ultrasound energy below the skin surface to stimulate the body's creation of new collagen, the natural protein that gives skin its youthful and wrinkle-free look. Known focused ultrasound therapy techniques are usually applied to lift such body parts as the face, chin, neck, and brows. As ultrasound can be used also in imaging, it is possible to first target the focused ultrasound energy towards the tissue layers where the collagen resides before treatment.

GENERAL DESCRIPTION

The presently disclosed subject matter provides an ultrasound-based tissue treatment technique that utilizes standard ultrasound devices, in contrast to the focused ultrasound techniques that require special designs of ultrasound devices/transducers which can become complicated and expensive, in addition to the need for professionals to operate them. Conversely, the devices disclosed herein are relatively simple to use and consequently can be used even in home-based environments.

As mentioned above, the essential purpose is to heat the tissue to damage the old collagen and elastin such that a healing process is initiated to produce new young collagen and elastin that substitute for the older ones. It is important that the heating of the tissue achieves the desired result by penetrating to the correct depth into the tissue and raising the temperature of the tissue to an effective and useful value/range.

Accordingly, the presently disclosed subject matter focuses on a device configured to be inserted between the tissue to be treated and a typical ultrasound device that can be used to treat the tissue, the device comprising at least one region which is heated to a certain temperature, within a predetermined temperature range, due to ultrasound energy interacting therewith, such that when the region is positioned in vicinity with the tissue, it heats the tissue being in direct or indirect contact, by heat diffusion, up to a certain temperature range and down to a certain tissue depth.

In some embodiments, the devices disclosed herein enable fractional (skin) tissue treatment by heating and damaging discrete portions of the (skin) tissue, but sufficient to initiate the healing process, while preserving the remaining portions of the (skin) tissue.

In some embodiments, the at least one region is made mainly from echo-resistive material(s).

In some embodiments, the at least one region extends over the whole cross section (width and depth) of the active portion of the device. In some embodiments, the at least one region extends along the whole height of the active portion of the device.

In some embodiments, the device includes attachment means to attach it to the ultrasound device. In some embodiments, the device includes attachment means to attach it to the (skin) tissue to be treated.

In some embodiments, the at least one region is formed as a protrusion/bump on the side of the region that faces the (skin) tissue and engages with the (skin) tissue during the treatment, such that when the device is attached to the tissue the at least one region is fully surrounded by tissue; this increases the heat transfer and facilitates the heat transfer into deeper layers of the (skin) tissue, whenever desired, due to the squeezing of the tissue layers. In some embodiments, the at least one region can be shiftable along a predetermined axis (e.g., perpendicularly to the (skin) tissue surface) to enable different degrees of engagement with the (skin) tissue.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION

Figure 1:
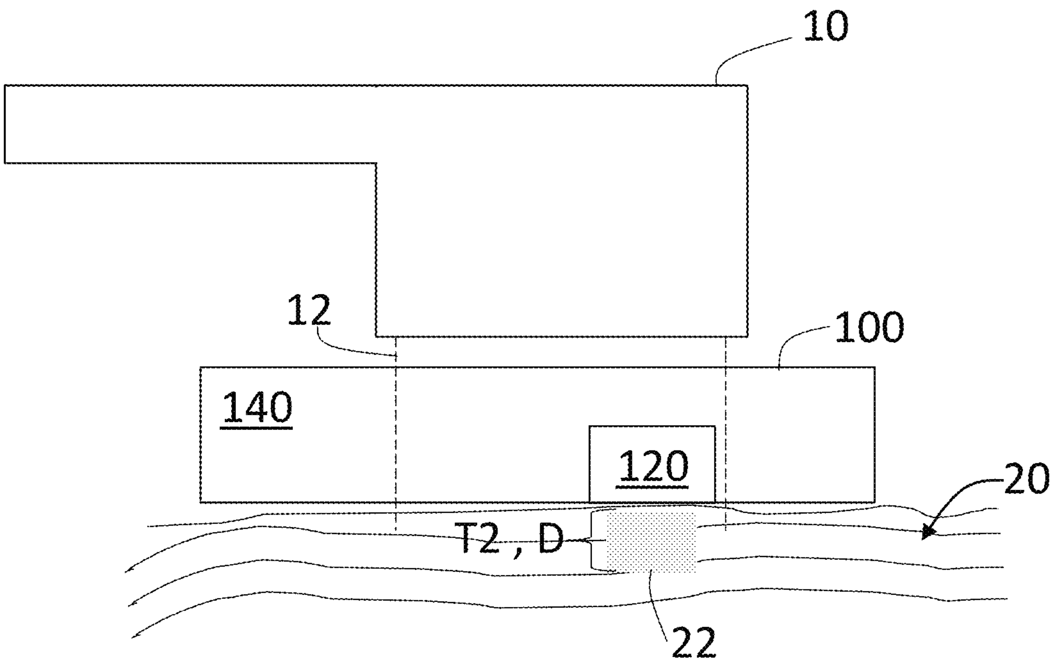
FIG. 1 illustrates a non-limiting exemplary embodiment of a device according to the present invention.

Reference is made to FIG. 1 illustrating, in a schematic and block diagram, a non-limiting example of a side view of a device 100 in accordance with a first non-limiting embodiment of the invention. As shown, the device 100 is located between an ultrasound (US) device 10 that generates an US beam/field 12, and tissue 20, usually skin tissue, although other tissues can be treated as well. The device 100 is configured for enhancing the treatment provided to the tissue 20 by the US device 10. In particular, the device 100 is configured to enhance the heating of the tissue 20 to cosmetically treat various conditions of the tissue 20, such as reducing wrinkles and tightening the skin.

The device 100 includes at least one region 120 that, when subjected to US beam/field having certain properties, such as frequency and intensity, is heated to a certain temperature T1, within a predetermined temperature range, due to interaction with the US beam/field. When the region 120 is positioned in vicinity of the skin tissue 20 it heats the skin tissue being in direct or indirect contact, by heat diffusion, up to a temperature range T2 and down to a certain tissue depth D. The temperature T2 and depth D are configured for treatment of one or more conditions of the tissue 20. Accordingly, the region 120 can be referred to herein as the treatment region of the device 100.

The device 100 is configured to provide a predetermined heating profile, characterized by temperature gradient and depth, inside the treated tissue 20, when the device 100 and the region 120 therein is subjected to a specific US beam having specific parameters, such as the frequency of each pulse, the intensity of each pulse, the US wavelength, the number of pulses in a train pulse, the frequency of pulses in a train pulse, a continuous (non-pulsed) wave, etc.

The at least one region 120 has a shape configured to provide the desired treatment to the treated tissue. In some embodiments, the region 120 has a large contact surface with the tissue. In some embodiments, the region 120 has a small/point contact surface with the tissue.

In some embodiments, the region 120 extends over the whole cross section (width and depth) of the active portion of the device, i.e. across the whole contact surface of the device with the tissue. In some embodiments, the at least one region extends along the whole height of the active portion of the device from the top to the bottom surface.

In some embodiments, the region 120 is made from an echo-resistive material. In this construction, the region 120 provides high resistance to the US beam passing therethrough and therefore heats according to a specific heat gradient due to interaction with the US beam. Non-limiting examples of echo-resistive materials include Glycerin and various mineral oils.

Echo-resistivity of the region 120 affects the region heating and consequently affects the heating profile in the treated tissue. A higher echo-resistivity results in more heating of the region 120 and the temperature of the contacted tissue will increase to a higher temperature at the surface and to a larger gradient and/or depth than when a lower echo-resistivity is utilized.

In the case where the region 120 does not cover the whole contact surface of the device 100 with the tissue 20, i.e. the region covers part of the device's contact surface with the tissue, the remaining part of the device 100 is made from a echogenic material 140 that is conductive to US and therefore does not heat controllably or excessively. The tissue which is contact with the echogenic part 140 of the device 100 will then not heat or will heat to a lesser degree than the tissue that is subjected to the heat diffusion caused by the heated region 120. Non-limiting examples of echogenic material include water-based gels, e.g. ultrasound gels.

In some embodiments, at least part of the device 100 is made from a rigid material. In some embodiments, at least a part of the device 100 is made from a flexible material. In some embodiments, when the region 120 extends over the whole cross section of the active portion (contact surface) of the device 100, the region 120 can be an echo-resistive gel that is stretched over the treated tissue. In some embodiments, air can be used instead of an echogenic material, e.g. the device 100 has a hollow shape (e.g. a cylinder) where the external wall forms the echo-resistive material and the hole inside the walls forms the echogenic material. In this example, the treatment region may follow a closed route, such as a ring.

In some embodiments, the US heating properties of the treatment region 120 are adjustable. In one example, the region 120 is made from a material that heats differently in response to different US beam properties, such as the US wavelength, its frequency, its intensity, etc. In another example, the region 120 is a compartment within the device 100 that can be filled with different echo-resistive materials, such as echo-resistive gels. In one example, the region 120 accepts replaceable cartridges carrying different materials having different echo-resistive properties. The region(s) 140 can also be configured as compartment(s)/replaceable cartridge(s) that accept(s) different liquid-based/gel-based materials.

In some embodiments, the device 100 includes attachment means to attach it to the US device 10. In some embodiments, the device 100 includes attachment means to attach it to the skin tissue to be treated. For example, the device 100 may have an adhesive surface to attach it to the skin surface.

The US device 10 can include one or more US transducers that generate the US beam(s). In some embodiments, the device 100 includes one or more treatment regions 120 that are coupled to one or more US transducers respectively. In some embodiments, a single treatment region 120 is coupled to a plurality of US transducers. In some embodiments, a plurality of treatment regions 120 are coupled to a single US transducer.

Figure 2A:
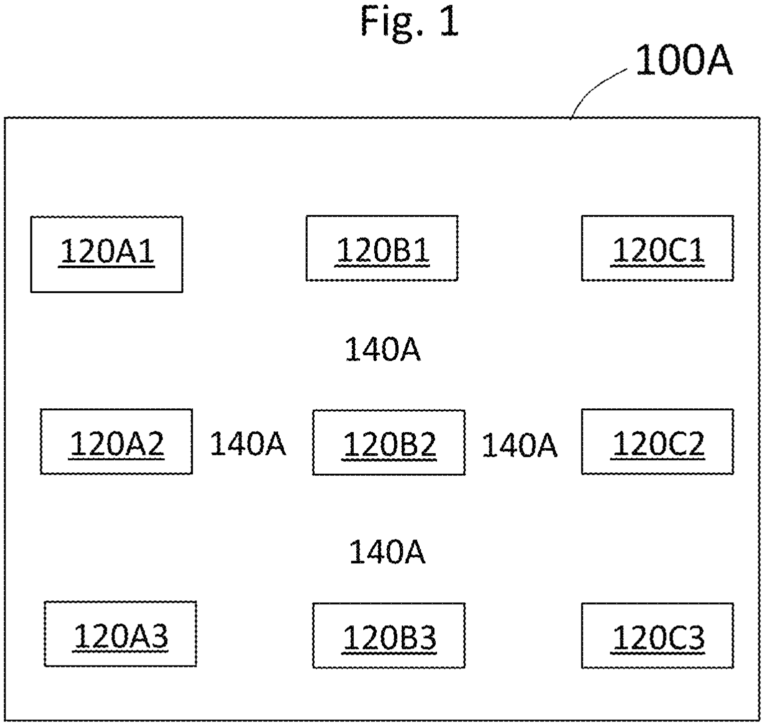
FIGS. 2A-2B illustrates another non-limiting exemplary embodiment of a device according to the invention, for fractional tissue treatment applications.
Figure 2B:
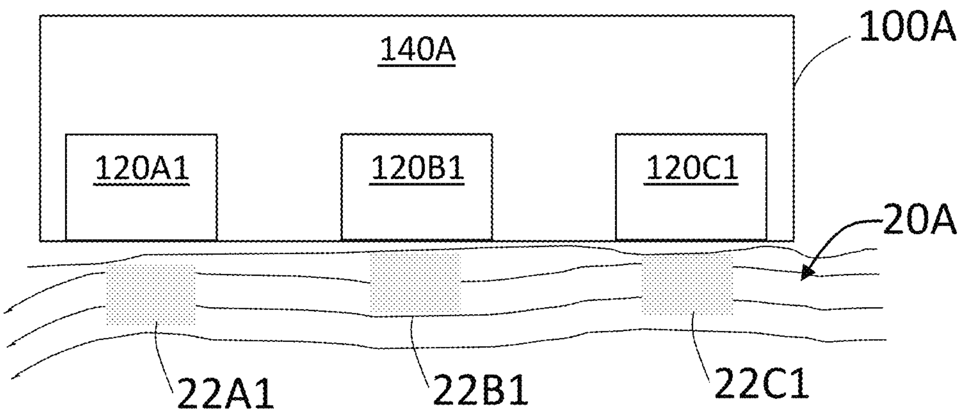

Reference is made to FIGS. 2A-2B showing a non-limiting example of a device 100A according to a non-limiting embodiment of the presently disclosed subject matter. In the example shown, the device 100A includes a plurality of regions (120A1-120C3) configured similarly to region 120 and one or more regions 140A configured similarly to region 140. In FIG. 2A, a bottom view of the device 100A is shown and illustrates an array of nine treatment regions 120A1-120C3 that are distributed over the bottom surface of the device 100A that is placed in contact with the treated tissue and are separated by the region 140A extending between them. This configuration enables multiple treatment spots in the tissue. In other words, the device 120A enables fractional skin tissue treatment by heating discrete portions of the skin tissue, enough to initiate the healing process, while preserving the rest of the skin tissue located therebetween, as shown in FIG. 2B depicting a side view of the device 100A and the corresponding heated tissue portions 22A1-22C1 within the tissue 20A. It is to be understood that the treatment regions 120A1-120C3 and the separating non-treated region 140A can be switched into another structural embodiment of the device. It is also noted that, when the device includes a plurality of the treatment regions, the latter can be configured with different materials having different echo-resistive properties to thereby differently treat the respective different tissue portions.

Figure 3A:
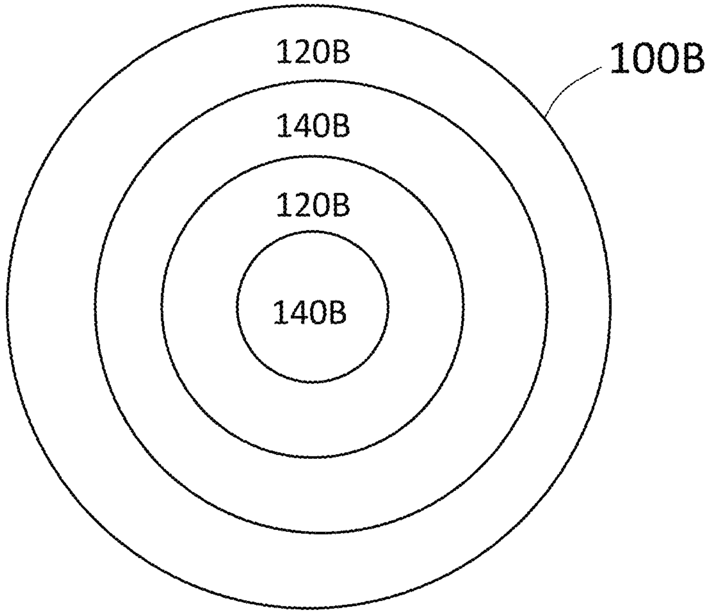
FIGS. 3A-3B show non-limiting exemplary embodiments of the device described in FIGS. 2A-2B.

Reference is made to FIGS. 3A-3 showing different non-limiting shapes of the device 100, the treatment regions 120 and the separating echogenic region.

In FIG. 3A, a bottom view of a device 100B, the contact surface of the device 100B, is shown as a circular shape. The contact surface includes several rings of treatment regions 120B separated by echogenic regions 140B. In this specific configuration, the cross section of the treated tissue, in a plane parallel to the tissue surface, will be two rings one inside the other and separated by a third ring.

Figure 3B:
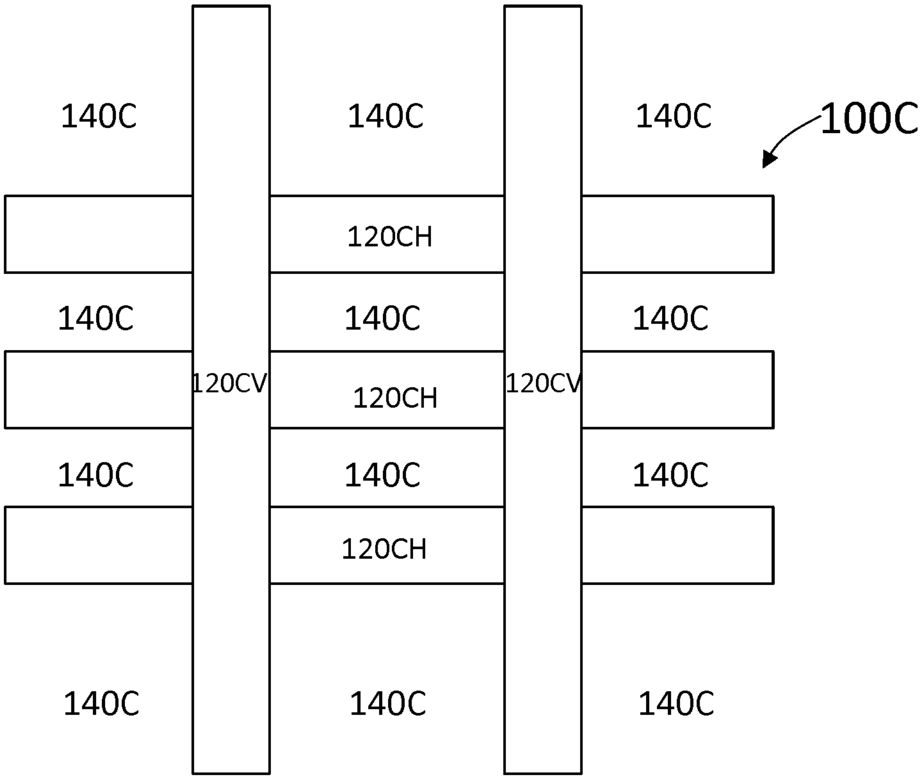

In FIG. 3B, a bottom view of a device 100C, illustrating a grid shaped contact surface 100C. As shown, three horizontal bars 120CH are crossed by two vertical bars 120CV. The horizontal and vertical bars are made from echo-resistive material and separated by echogenic regions, or air.

It may be appreciated that many other shapes for the device can be introduced. FIGS. 3A-3B show two of the shapes that can be used with an US device for fractional treatment of the skin.

Figure 4:
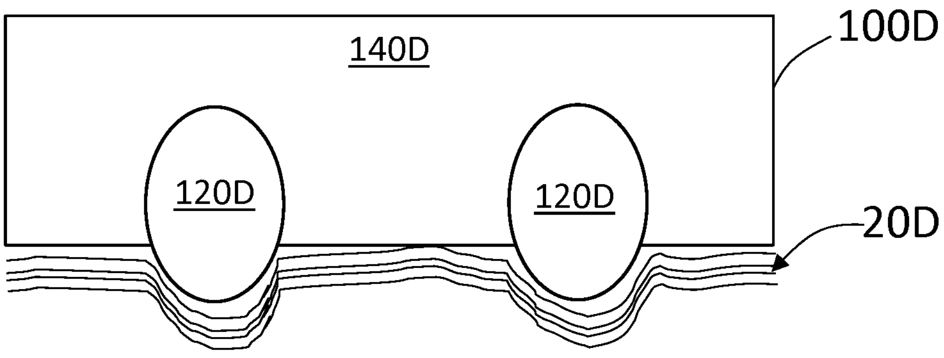
FIG. 4 illustrates a non-limiting example of a device having the treatment regions projecting downwardly from the bottom surface of the device, according to exemplary embodiments of the invention.

Reference is made to FIG. 4 illustrating another non-limiting example of a device 100D according to some non-limiting embodiments of the presently disclosed subject matter. As shown in a side view, a device 100D includes two treatment regions 120D separated by the remaining, non-treatment, region 140D of the device. In this example, the treatment regions 120D project downwardly from the bottom surface of the device 100D and form protrusions/bumps that face the treated tissue and engage with the skin tissue during treatment. This enables better coupling between the regions 120D and the tissue 20D at the specific points. In addition, this configuration can increase the area of the treated tissue that surrounds the treatment region and can facilitate heat transfer to the tissue due to the larger contact surface and the squeezing of the tissue layers. In some embodiments, the region 120D can be movable by a suitable mechanism (not shown) along a predetermined axis (e.g., perpendicularly to the skin tissue surface) to enable different degrees of downward projection into the skin tissue and varied engagement with the tissue. It also may be appreciated that different regions 120D can be projected differently in order to adapt to contour of the treated tissue and the body part.

The invention claimed is:

1. A device configured to be inserted between a tissue to be treated and an ultrasound (US) device that can be used to treat the tissue, the device comprising at least one region configured to be heated to a certain temperature, inside a predetermined temperature range, due to the action of the ultrasound device of predetermined properties interacting therewith, configured such that when the at least one region is positioned in a vicinity of the tissue, the action of the ultrasound device heats the tissue, by heat diffusion, according to a heating profile characterized by a temperature range and a tissue depth.

2. The device according to claim 1, comprising a plurality of said regions being spaced-apart over a bottom surface of the device, thereby enabling a fractional treatment of the tissue when being heated by the action of the ultrasound device.

3. The device according to claim 1, wherein said at least one region is in the form of a fixed or replaceable compartment configured to be filled with different materials having different heating reactions to the application of ultrasound energy, thereby enabling respective different heating profiles of the tissue.

4. The device according to claim 1, wherein said at least one region is configured to project downwardly from a bottom surface of the device, thereby enabling deeper engagement with and heating of the tissue.

5. The device according to claim 1, wherein said at least one region is comprised of one or more echo-resistive materials.

6. A system for treating tissue, comprising:

the device of claim 1; and the ultrasound device configured and operable to generate ultrasound energy of the predetermined properties.

7. A method of treating tissue with an ultrasound (US) device comprising:

inserting a device between a tissue to be treated and the ultrasound device configured to treat the tissue, wherein the device comprises at least one region;

placing the at least one region in a vicinity of the tissue;

heating the at least one region to a predetermined temperature range, due to US energy having predetermined properties interacting therewith; and heating the tissue in the vicinity of the at least one region by heat diffusion of the at least one region, wherein the heating of the tissue is according to a heating profile defined by a temperature range and a tissue depth.

* * * * *